(12) United States Patent
Kleiman et al.

(10) Patent No.: US 6,757,416 B2
(45) Date of Patent: Jun. 29, 2004

(54) DISPLAY OF PATIENT IMAGE DATA

(75) Inventors: Felix Kleiman, Haifa (IL); David Maier Neustadter, Cleveland, OH (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 531 days.

(21) Appl. No.: 09/729,601

(22) Filed: Dec. 4, 2000

(65) Prior Publication Data

US 2002/0068862 A1 Jun. 6, 2002

(51) Int. Cl.$^7$ .............................................. G06K 9/00
(52) U.S. Cl. ..................................... 382/131; 382/103
(58) Field of Search ................................ 382/103, 128, 382/131, 132; 348/77, 164, 169; 378/205, 207; 600/414, 417, 426, 429; 606/130

(56) References Cited

U.S. PATENT DOCUMENTS

| | | | |
|---|---|---|---|
| 5,617,857 A | 4/1997 | Chader et al. | 128/653.1 |
| 5,622,170 A | 4/1997 | Schulz | 128/653.1 |
| 5,947,900 A | 9/1999 | Derbyshire et al. | 600/410 |
| 5,961,456 A | 10/1999 | Gildenberg | 600/429 |
| 6,006,126 A * | 12/1999 | Cosman | 600/426 |
| 6,246,898 B1 * | 6/2001 | Vesely et al. | 600/424 |
| 6,351,661 B1 * | 2/2002 | Cosman | 600/426 |
| 6,675,040 B1 * | 1/2004 | Cosman | 600/427 |

OTHER PUBLICATIONS

Kormos, et al. "Intraoperative, real–time 3–D digitizer for neurosurgical treatment and planning", IEEE, p. 1258, 1993.*
Freiherr "Providing the power behind virtual reality", and Adam, et al. "An optical navigator for brain surgery", MDL, pp. 1–10, 1997.*
Adams, et al. "An optical navigator for brain surgery", and Adams, et al. "An optical navigator for brain surgery", IEEE, pp. 48–50 1996.*
Magnetic Resonance Imaging, printed from Internet address http://www.ge.com/medical/mr/iomri/index.html on Apr. 27, 2000, 1 page.
Polaris Optical Tracking System, printed from Internet address http://www.ndigital.com/polaris.html on May 8, 2000, 3 pages.

* cited by examiner

Primary Examiner—Daniel Mariam
(74) Attorney, Agent, or Firm—Foley & Lardner LLP; Michael A. Della Penna; Peter J. Vogel

(57) ABSTRACT

A method of generating display signals for the presentation of patient image data for a caregiver includes receiving caregiver location data representing the location of a caregiver's head, receiving patient image data representing a subject region of a patient, and generating display signals based on the patient image data and the caregiver location data.

23 Claims, 4 Drawing Sheets

DISPLAY OF PATIENT IMAGE DATA

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The present invention relates generally to the field of patient image acquisition and display. The present invention relates more specifically to more intuitive and convenient display of patient images.

BACKGROUND OF THE INVENTION

Patient image acquisition has become increasingly important in medical diagnostics and disease treatment. Common imaging techniques include magnetic resonance imaging (MRI), open-magnet MRI, computer tomography (CT), X-RAY, etc. One use of open-magnet MRI is in interventional neuroradiology. Interventional neuroradiology is a minimally invasive approach to the treatment of vascular diseases of the central nervous system.

Interventional neuroradiology requires real-time imaging in which a caregiver (e.g., a surgeon) performing an interventional procedure has direct visual contact with a subject region of a patient and with a display of the real-time MRI image of that subject region. Naturally, an accurate and easily adjustable image of the subject region is required for the caregiver to properly treat the patient.

One difficulty caregivers have encountered with such real-time imaging systems is that the orientation of the image can be confusing. The orientation of the image is often different than the orientation in which the caregiver sees the patient. For example, a sagittal MRI image is conventionally displayed with the top of the patient's head corresponding to the top of the image. While this orientation may be convenient for some standard radiological and diagnostic uses of MRI, it can be very confusing when the images are presented to a caregiver who is simultaneously looking at a patient during an interventional procedure. In an interventional procedure, the caregiver sees the patient lying down and therefore would see the sagittal slice with the top of the head to one side.

Current methods of slice localization for real-time imaging include interactive real-time imaging interfaces in which an operator sits at a console and modifies the slice prescription using some sort of input device such as a mouse or track ball. However, this method does not orient the image to correspond to the view of the caregiver relative to the subject area of the patient. Another method which has been implemented includes using a hand-held pointer that is tracked by a tracking device in or near the imaging volume of the subject region. The tracking device provides an input to a slice localization system, and the slice localization system selects a slice which includes the tip of the pointer. This method also fails to orient the image to correspond to the view of the caregiver relative to the subject area of the patient.

Accordingly, what is needed is a system and method for patient image display which includes variable orientation of the patient image. Further what is needed is such a system and method which overcomes the problems associated with a patient image having a different orientation than that of a caregiver relative to the subject area of the patient. Further still, what is needed is a more intuitive and convenient method for displaying real-time patient images to a caregiver during interventional medical techniques or when a caregiver views images at a workstation.

BRIEF SUMMARY OF THE INVENTION

According to one exemplary embodiment, a method of generating display signals for the presentation of patient image data for a caregiver includes receiving caregiver location data representing the location of a caregiver's head, receiving patient image data representing a subject region of a patient, and generating display signals based on the patient image data and the caregiver location data.

According to another exemplary embodiment, a system for generating display signals for the presentation of patient image data includes a tracking device, an imaging device, and a computer. The tracking device is configured to track the location of a caregiver's head with respect to a subject region of a patient and to generate location data based on the tracked location. The imaging device is configured to acquire an image of a patient and to generate patient image data based on the image. The computer is configured to receive the location data and the patient image data and to generate display signals based on the patient image data. The display signals have an orientation representing the orientation of the caregiver's head with respect to the subject region.

According to yet another exemplary embodiment, a tracking system for generating caregiver location data for a patient imaging system includes a reference target, a mounting, and a locator. The mounting is configured for securing the reference target in the vicinity of a caregiver's head. The locator is configured to communicate with the reference target in real time to locate the reference target and to generate caregiver location data based thereon.

According to still another exemplary embodiment, a system for generating display signals for the presentation of patient image data for a caregiver includes means for receiving caregiver location data representing the location of a caregiver's head; means for receiving patient image data representing a subject region of a patient; and means for generating display signals based on the patient image data and the caregiver location data.

BRIEF DESCRIPTION OF THE DRAWINGS

The invention will become more fully understood from the following detailed description, taken in conjunction with the accompanying drawings, wherein like reference numerals refer to like parts, in which.

DETAILED DESCRIPTION OF EXEMPLARY EMBODIMENTS

Figure 1:
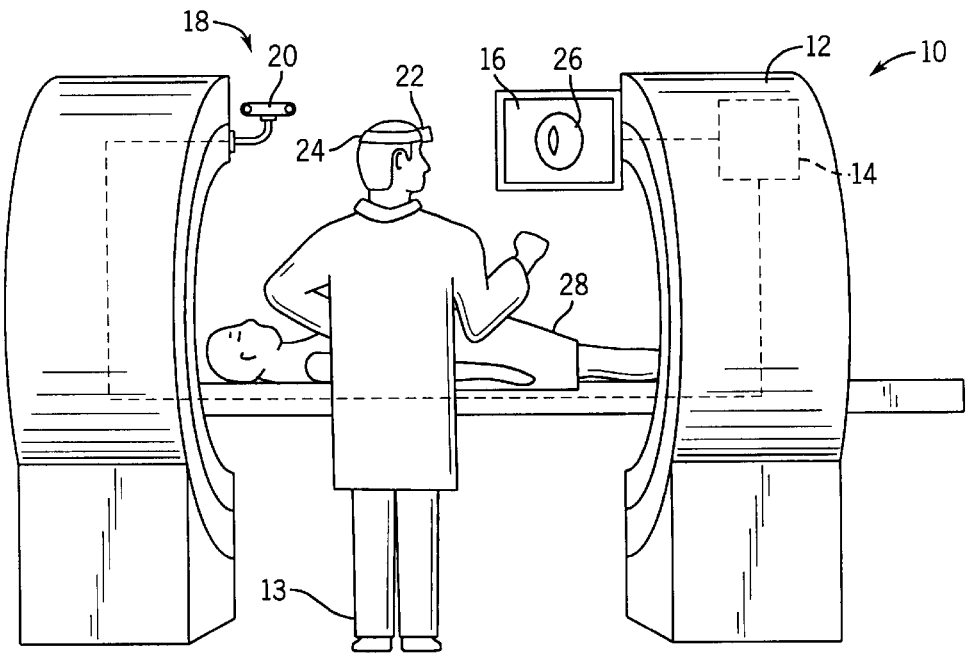
FIG. 1 is a diagram of a patient imaging system according to an exemplary embodiment.

Referring first to FIG. 1, a patient image display system 10 is shown implemented on an open-magnet MRI device 12 according to an exemplary embodiment. Open-magnet MRI device 12 is a Signa SP Magnetic Resonance Imaging system manufactured by GE Medical Systems, Milwaukee, Wis., but may alternatively be other types of patient imaging systems. The Signa SP allows a caregiver 13 (e.g., a surgeon, a radiologist, etc.) to perform a wide variety of procedures while viewing the position of the caregiver's instruments in relation to organs and structures inside the body.

Display system 10 includes a computer 14, a display 16, and a tracking device 18. Tracking device 18 includes a locator 20, a reference target 22, and a mounting 24 in this exemplary embodiment. Computer 14 includes a microprocessor, memory, input/output devices, and/or other digital or analog circuitry necessary to carry out the functions described herein. Display 16 includes full-color, active matrix, liquid crystal display (LCD) technology in this exemplary embodiment, but may alternatively be any type of display, including other LCDs, cathode ray tubes (CRTs), light-emitting diode (LED) displays, television screens, etc. Computer 14 is configured to generate display signals based on patient image data and to transmit the display signals to display 16.

Computer 14 performs two functions in this exemplary embodiment: imaging and tracking. Imaging includes utilizing MRI device 12 to generate an image 26 of a selected slice of a patient 28, using known magnetic resonance imaging techniques and displaying the selected slice on display 16. Tracking includes tracking the location of the head of caregiver 13 in real time by tracking reference target 22. The location may be tracked relative to a reference point, a fixed point, or in absolute positioning. In this exemplary embodiment, the location of the head of caregiver 13 is tracked relative to the MRI device 12 reference frame and computer 14 then calculates the position relative to the acquired slice. Computer 14 then adjusts the orientation of the image data represented by the display signals (e.g., rotational orientation, flip, etc.) provided to display 16 based upon the location of reference target 22. Computer 14 may further generate the display signals based on the caregiver location data by adjusting the angular orientation of the acquired image. Alternatively, separate computers may be used for each of imaging and tracking.

Figure 2:
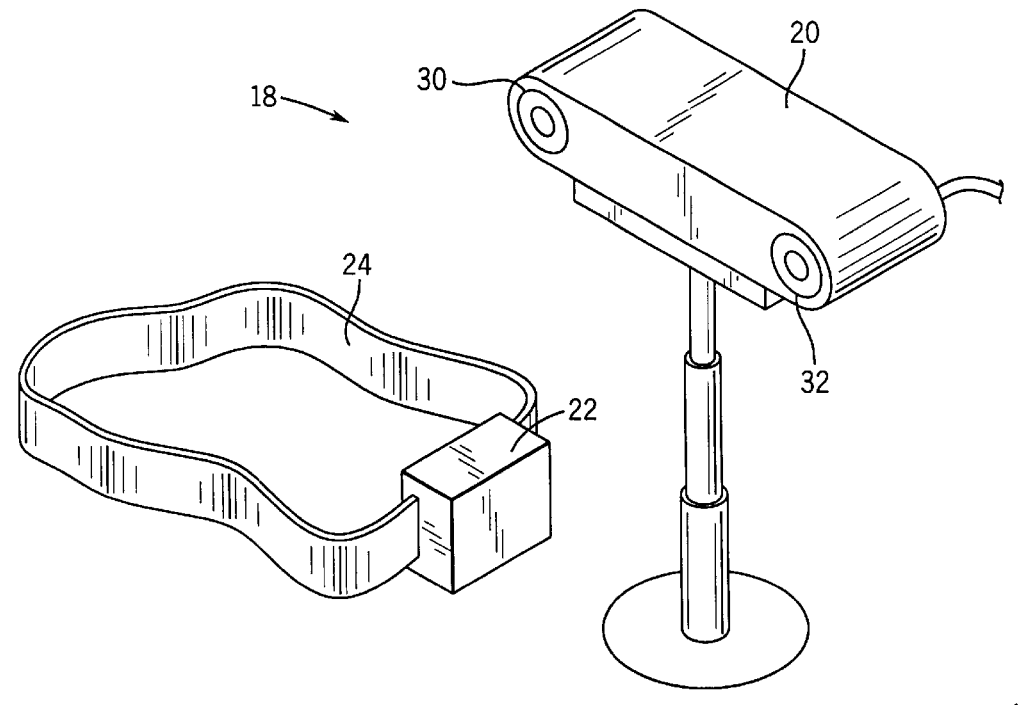
FIG. 2 is a diagram of a tracking system according to an exemplary embodiment.

Referring to FIG. 2, an exemplary tracking device 18 is shown. In this exemplary embodiment, tracking device 18 is a Passive Polaris Optical Tracking System, manufactured by Northern Digital Inc., Waterloo, Ontario (Canada). Tracking device 18 includes locator 20, reference target 22, and mounting 24. Locator 20 includes a transmitter 30 and a receiver 32. Reference target 22 includes multiple retro-reflective objects, such as spheres or disks. Locator 20 transmits optical signals which are reflected off the reflective material and which return to locator 20. In conjunction with application software, locator 20 is configured to determine real time positions and orientations (6 degrees of freedom) of reference target 22. Alternative tracking devices may be used, including active and passive optic tracking devices, electromagnetic tracking devices, light-emitting diodes (LEDs), video cameras, etc.

Reference target 22 is coupled to a mounting 24 adapted for securing reference target 22 in the vicinity of a caregiver's head. Reference target 22 is mounted so that movements of the caregiver's head generates corresponding movements of reference target 22. Mounting 24 is shown as an elastic strap in this exemplary embodiment, but may alternatively be any other type of mounting, such as a leather strap, a hat, an adhesive, etc.

Figure 3:
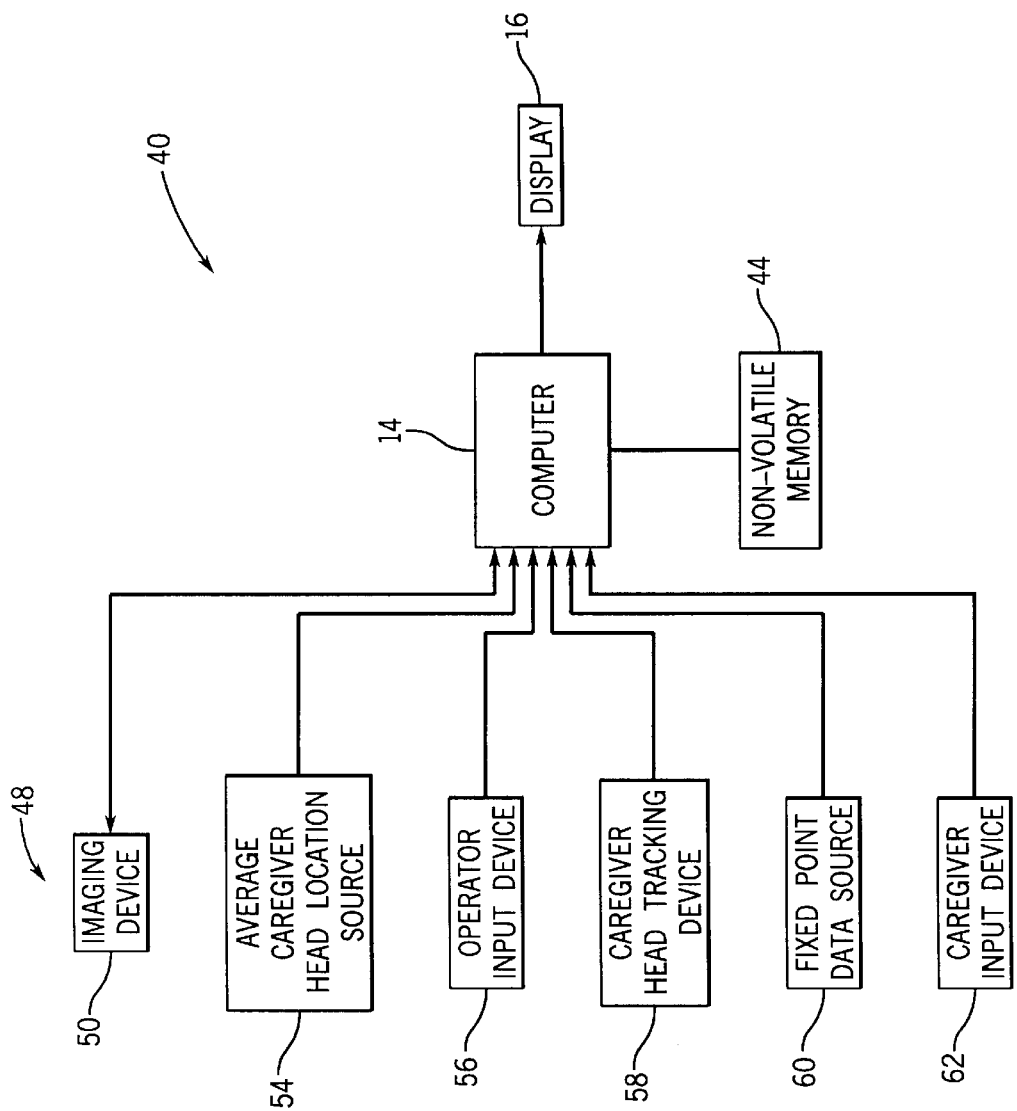
FIG. 3, is a flow diagram of a patient image display system according to an exemplary embodiment.

Referring now to FIG. 3, a flow diagram is shown illustrating multiple embodiments of a patient image display system 40. System 40 includes computer 14, non-volatile memory 44, and display 16. System 40 further includes a plurality of input sources 48. As will become clear, not all of input sources 48 are required for each embodiment of system 40.

An imaging device 50 includes any medical imaging device, such as, MRI, ultrasound (US), computerized tomography (CT), X-ray, positron emission tomography (PET), photon emission computerized tomography (SPECT), etc. Imaging device 50 is configured to provide image data, for example, in the form of an image slice, to computer 14. Alternatively, imaging device 50 and computer 14 may share common processing elements (e.g., memory, microprocessor, etc.).

An average caregiver head location source 54 includes an input device or a memory location configured to provide average caregiver head location data to computer 14. For example, the memory location may include the position of an average caregiver's head, such as, at magnet isocenter along the Z axis of the patient, 60 degrees above the horizontal in the X-Y plane. Alternatively, a human operator could provide the caregiver height via an input device 56, such as a keyboard, mouse, track ball, touch screen, etc.

A caregiver head tracking device 58 is any device suitable for tracking the position of a caregiver's head, such as that shown and described with reference to FIG. 3.

Figure 5:
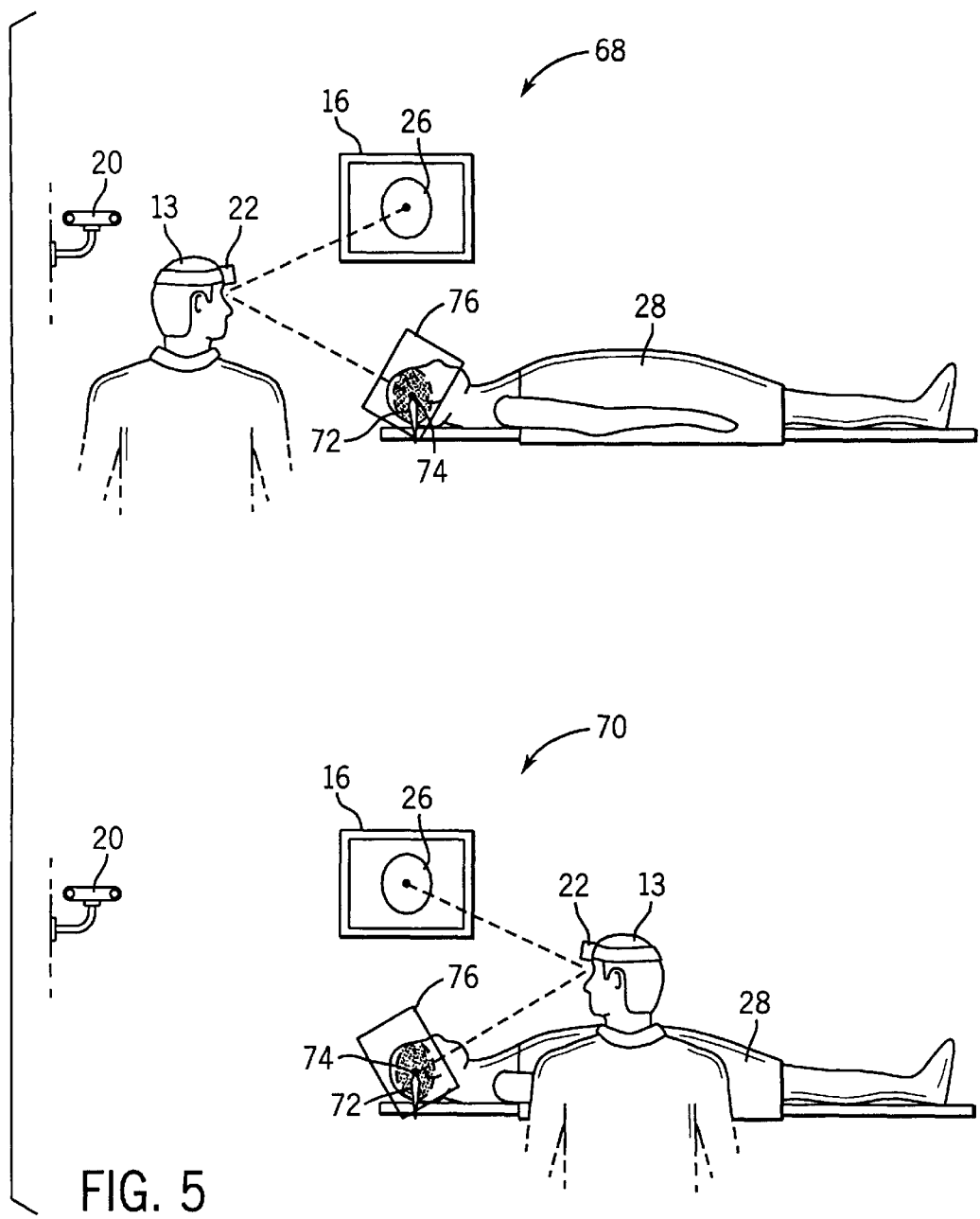
FIG. 5 shows two sketches illustrating a second exemplary embodiment.

Fixed point data source 60 includes an input device or a memory location configured to provide a fixed point through which a perpendicular relationship is maintained between the line of sight of the caregiver and the patient image data (see FIG. 5). Fixed point data source 60 may be defined by selection on a previous image (e.g., the center of a tumor), wherein the fixed point data is stored in a non-volatile memory such as memory 44, or by a tracking device (e.g., the tip of a pointer).

Caregiver input device 62 includes a wireless or wired foot pedal or pushbutton accessible by the caregiver to provide a "display hold" signal to computer 14, wherein the display hold signal causes computer 14 to hold the state of the image data in the display signals without reference to continuing changes in the caregiver location data.

According to a first embodiment, the rotational orientation (including flip) of an image (e.g., an image slice) is adjusted so that the resulting image is in the same orientation as the caregiver sees the patient directly. Caregiver head location data is received from average caregiver head location source 54, which may be a memory location in non-volatile memory 44. In this exemplary embodiment, caregiver head location data represents an average caregiver head location. For example, an average caregiver head location may be at magnet isocenter along the Z axis of the patient, 60 degrees above the horizontal in the X-Y plane. Other coordinate systems may be utilized to express the position of the average caregiver's head relative to the subject region of the patient. Alternatively, a human operator, perhaps controlling a portion of the imaging process in another room, may utilize input device 56 to input the caregiver's head location or caregiver's height to computer 14, or the caregiver's head location may be tracked using caregiver head tracking device 58.

Computer 14 receives patient image data from imaging device 50 representing a subject region of a patient and generates display signals based on the patient image data and the caregiver head location data. Computer 14 adjusts the rotational orientation (including flip, if necessary) of the patient image data based on the caregiver location data.

Figure 4:
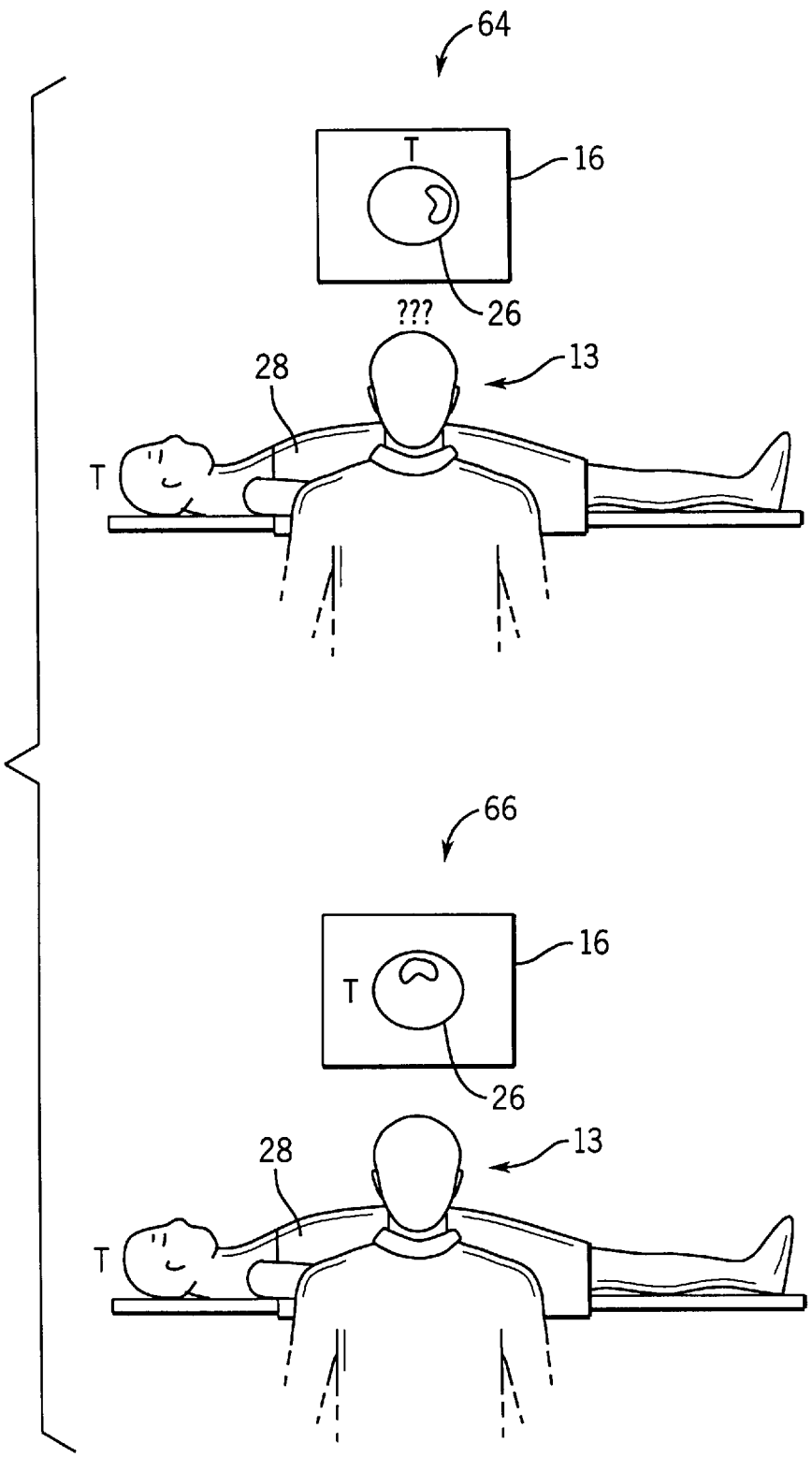
FIG. 4 shows two sketches illustrating a first exemplary embodiment.

With reference to FIG. 4, a sketch of this embodiment is shown. In a first sketch 64 before implementation of this exemplary embodiment, caregiver 13 sees a different rotational orientation of image 26 in display 16 than that of patient 28, leading to confusion. Note that "T" indicates the top of the head of patient 28. In a second sketch 66 after implementation of this exemplary embodiment, image 26 takes into consideration the location of caregiver 13 and adjusts the orientation of image 26 such that the same rotational orientation is maintained between image 26 and the head of patient 28.

According to a second exemplary embodiment, the caregiver's head position is further used to determine the angular position of the image such that the image slice is always positioned to pass through a fixed point in the imaging volume and to be perpendicular to the line of sight of the caregiver. Thus, computer 14 receives fixed point data from source 60 which represents the location of the tip of a pointer (e.g., a biopsy needle) which is tracked with a tracking device. Fixed point data 60 may alternatively represent another fixed point, such as, a point of interest in the subject region (e.g., the center of a tumor) wherein the data is retrieved from a non-volatile memory. In this way, by moving the head, the caregiver can rotate the slice around the fixed point, viewing the region of interest from different angles.

With reference to FIG. 5, a sketch of this embodiment is shown. In a first sketch 68, a pointer 72 is used to select a fixed point 74 of a subject region of patient 28. Computer 14 is configured to track the location of the head of caregiver 13 using locator 20 and reference target 22, wherein reference target 22 is mounted to the head of caregiver 13. Computer 14 is further configured to select and acquire a real-time image from imaging device 50 of a slice of patient 28. Computer 14 selects the desired image by sending control signals to imaging device 50. Computer 14 selects a slice passing through fixed point 74 and in a plane 76 perpendicular to the line of sight of caregiver 13. Computer 14 then generates display signals to produce an image on display 16 that has an angular and rotational orientation corresponding to the view the caregiver 13 sees of the subject region of patient 28. As caregiver 13 moves from one location to another, computer 14 is configured to update in real time the image slice of patient 28 which is acquired and displayed. As shown in second sketch 70, computer 14 commands imaging device 50 to move plane 76 as caregiver 13 moves so that plane 76 includes fixed point 74 and maintains a perpendicular relationship with the line of sight of the caregiver. Further, as pointer 72 is moved from one location to another, computer 14 is configured to command imaging device 50 to update the image slice of patient 28 in a similar manner.

According to one alternative embodiment, display 16 may be a head-up display mounted on the caregiver's head (or glasses) which allows the caregiver to view the patient and the display simultaneously or with very little movement of the eyes. This provides a significant advantage when the caregiver's head position is being used to determine the slice orientation because it allows the caregiver to move his/her head while maintaining the same convenient eye contact with the display.

According to one advantageous feature, caregiver 13 has access to caregiver input device 62 (e.g., a push-button, a hand-held device, a foot pedal, etc.) while viewing the subject region of patient 28 which allows caregiver 13 to hold or "freeze" image 26 in position while caregiver 13 moves from one location to another. Input device 62 sends a "display hold" signal to computer 14 when actuated by caregiver 13. Upon receipt of the display hold signal, computer 14 holds the state of the display signals provided to display 16 without reference to continuing changes in the caregiver location data.

According to a third exemplary embodiment, the principles disclosed herein may be applied to use by a caregiver who is not also simultaneously viewing a patient. In this embodiment, a caregiver is viewing patient image data on a display (e.g., a workstation, such as a 3-dimensional workstation, a Picture Archiving Communications System (PACS) workstation, etc.) and can adjust the orientation (e.g., angular, rotational, etc.) by moving the caregiver's head. A locator is mounted on or near the display and the caregiver wears a reference target in the vicinity of the head to provide the tracking capability. The patient data may be provided from a database of three-dimensional patient data (e.g., stored in non-volatile memory 44), or may be provided in real time from a patient at a nearby location.

While the embodiments and application of the invention illustrated in the FIGS. and described above are presently preferred, it should be understood that these embodiments are offered by way of example only. For example, alternative tracking systems are contemplated. Further, additional applications are contemplated beyond specific examples of open-magnet MRI and workstation use provided herein. Accordingly, the present invention is not limited to a particular embodiment, but extends to various modifications that nevertheless fall within the scope of the appended claims.

What is claimed is:

1. In a computerized system, a method of generating display signals for the presentation of patient image data for a caregiver, comprising:
   receiving caregiver location data representing the location of the caregiver's head;
   receiving patient image data from an imaging device in real time, the patient image data representing a subject region of a patient; and
   generating display signals in real time based on the patient image data and the caregiver location data, including:
      receiving a fixed point on the patient image data; and
      adjusting the angular orientation of the display signals to maintain a perpendicular relationship between the location of the caregiver's head and the patient image data through the fixed point.

2. The method of claim 1, wherein the step of generating display signals includes adjusting the rotational orientation of the patient image data based on the caregiver location data.

3. The method of claim 2, wherein the step of receiving caregiver location data includes retrieving the caregiver location data from a non-volatile storage device, wherein the caregiver location data represents an average caregiver head location relative to the subject region of the patient.

4. The method of claim 2, wherein the step of receiving caregiver location data includes receiving caregiver height data from a human operator.

5. The method of claim 2, wherein the step of receiving caregiver location data includes tracking the location of the caregiver's head in real time.

6. The method of claim 1, wherein the step of receiving a fixed point on the patient image data includes tracking the location of the tip of a pointer to generate the fixed point.

7. The method of claim 1 wherein the step of receiving a fixed point on the patient image data includes retrieving the fixed point from a non-volatile storage device, wherein the fixed point represents a point of interest of the patient image data.

8. The method of claim 1, further comprising:
  receiving a display hold signal from an input device operable by the hand or foot of the caregiver; and
  upon receipt of the display hold signal, holding the state of the display signals without reference to continuing changes in the caregiver location data.

9. The method of claim 1, wherein the patient image data is displayed on a workstation.

10. The method of claim 9, wherein the workstation is a three-dimensional workstation.

11. A system for generating display signals for the presentation of patient image data, comprising:
  a tracking device configured to track the location of a caregiver's head with respect to a subject region of a patient and to generate location data based on the tracked location;
  an imaging device configured to acquire an image of a patient and to generate patient image data based on the image; and
  a computer configured to receive the location data and the patient image data and to generate display signals based on the patient image data and to adjust the angular orientation of the display signals based on the location data and a fixed point on the patient image data to maintain a perpendicular relationship between the location of the caregiver's head and the patient image data through the fixed point.

12. The system of claim 11, wherein the computer is configured to adjust the rotational orientation of the display signals.

13. A system for generating display signals for the presentation of patient image data for a caregiver, comprising:
  means for receiving caregiver location data representing the location of a caregiver's head;
  means for receiving patient image data from an imaging device the patient image data representing a subject region of a patient; and
  means for generating display signals based on the patient image data and the caregiver location data, including: means for receiving a fixed point on the patient image data; and means for adjusting the angular orientation of the display signals to maintain a perpendicular relationship between the location of the caregiver's head and the patient image data through the fixed point.

14. The system of claim 13, further comprising means for adjusting the rotational orientation of the patient image data based on the caregiver location data.

15. The system of claim 14, further comprising means for tracking the location of the caregiver's head in real time.

16. The system of claim 2, further comprising means for tracking the location of the tip of a pointer to generate the fixed point.

17. The system of claim 13, further comprising:
  means for receiving a display hold signal from an input device operable by the hand and foot of the caregiver; and
  upon receipt of the display hold signal, means for holding the state of the display signals without reference to continuing changes in the caregiver location data.

18. The system of claim 13, wherein the patient image data is displayed on a workstation.

19. The system of claim 18, wherein the workstation is a three-dimensional workstation.

20. In a computerized system, a method of generating display signals for the presentation of patient image data for a caregiver, the method comprising:
  receiving caregiver location data representing the location of the caregiver's head;
  receiving patient image data representing a subject region of a patient; and
  generating display signals based on the patient image data and the caregiver location data including:
    receiving a fixed point on the patient image data; and
    adjusting the angular orientation of the display signals to maintain a perpendicular relationship between the location of the caregiver's head and the patient image data through the fixed point.

21. A method according to claim 20, wherein the step of generating display signals further includes adjusting the rotational orientation of the patient image data based on the caregiver location data.

22. A method according to claim 21, wherein the fixed point represents a point of interest of the patient image data.

23. A method according to claim 21, wherein the patient image data is received from a database and displayed on a workstation.

* * * * *

UNITED STATES PATENT AND TRADEMARK OFFICE
CERTIFICATE OF CORRECTION

PATENT NO. : 6,757,416 B2 Page 1 of 1
DATED : June 29, 2004
INVENTOR(S) : Felix Kleiman and David Maier Neustadter It is certified that error appears in the above-identified patent and that said Letters Patent is hereby corrected as shown below:

<u>Title page,</u>
Item [*] Notice, delete "bydays.days." and substitute -- by 531 days. --.

<u>Column 6,</u>
Line 60, after "claim 1" insert -- , --.

<u>Column 7,</u>
Line 37, after "device" insert -- , --.

<u>Column 8,</u>
Line 6, after "claim," delete "2" and substitute -- 13 --.

Signed and Sealed this

Twelfth Day of October, 2004

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,757,416 B2 |
| DATED | : June 29, 2004 |
| INVENTOR(S) | : Felix Kleiman and David Maier Neustadter |

It is certified that error appears in the above-identified patent and that said Letters Patent is hereby corrected as shown below:

<u>Column 6,</u>
Line 63, after "claim 1" insert -- , --.

Signed and Sealed this

Twelfth Day of April, 2005

JON W. DUDAS
*Director of the United States Patent and Trademark Office*